United States Patent [19]

Moss

[11] 4,015,334
[45] Apr. 5, 1977

[54] POSTERIOR DIRECT BOND ORTHODONTIC UNIT SEGMENT

[76] Inventor: Dan Moss, 247 Ridge Road, Cedar City, Utah 84720

[22] Filed: Oct. 15, 1975

[21] Appl. No.: 622,604

[52] U.S. Cl. .............................................. 32/14 A
[51] Int. Cl.² ..................................... A61C 7/00
[58] Field of Search ................ 32/14 R, 14 A, 14 E

[56] References Cited

UNITED STATES PATENTS

| 2,502,902 | 4/1950 | Tofflemire | 32/14 A |
| 3,408,739 | 11/1968 | Johnson | 32/14 A |
| 3,639,986 | 2/1972 | Kesling | 32/14 A |
| 3,765,091 | 10/1973 | Northcutt | 32/14 A |
| 3,772,787 | 11/1973 | Hanson | 32/14 A |
| 3,903,604 | 9/1975 | Snead | 32/14 D |

Primary Examiner—Robert Peshock

[57] ABSTRACT

An orthodontic bracket is disclosed which is formed from an elongated section of metal that enables it to be directly bonded to the buccal surfaces of a plurality of the teeth. The bracket is attached to the buccal surfaces of the teeth by direct bonding to a plurality of contoured surfaces which have been formed from the elongated section of metal. A bent section is formed between each adjacent pair of contoured surfaces whose length is an approximate function of the distance between the centers of the teeth to which the adjacent contoured surfaces are attached. An archwire attachment is formed in each of the bent sections. Buccal and head gear tubes are attached to one of the bent sections.

16 Claims, 4 Drawing Figures

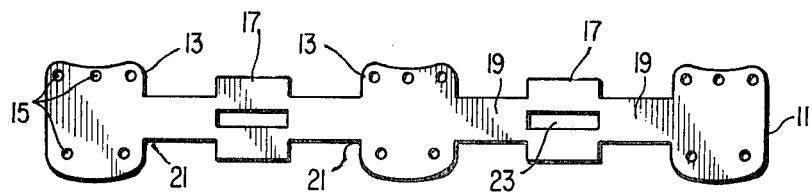
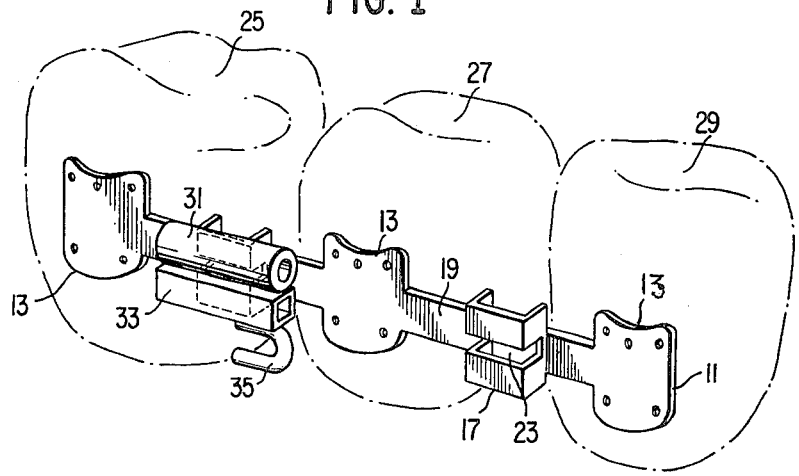
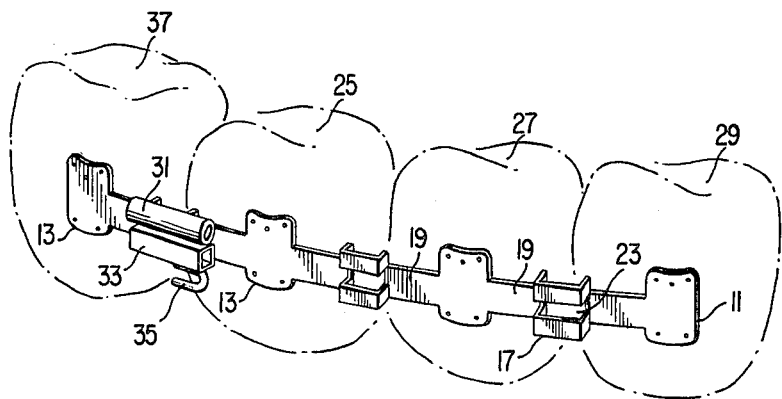

POSTERIOR DIRECT BOND ORTHODONTIC UNIT SEGMENT

BACKGROUND OF THE INVENTION

1. Field of the Invention

The invention relates to orthodontic brackets of the type which are directly bonded to the teeth. More particularly, the invention relates to a directly bonded orthodontic bracket of the type which is attached to more than one tooth.

2. Description of the Prior Art

Heretofore, orthodontic brackets have been attached separately to the individual teeth to which orthodontic correctional forces are to be applied. Individual attachment of orthodontic brackets by direct bonding or by attachment to orthodontic bands has several disadvantages. First, the physical attachment is time consuming thereby causing a decrease in the productivity of the orthodontist. Second, mastication forces often cause the individual brackets to break into pieces or the weld to break between the bracket and an orthodontic band to which the bracket is welded. Finally, it is often impossible to attach an individual orthodontic bracket to the second molars because they have not sufficiently erupted to permit the bracket surface to be attached to the tooth below the clinical crown.

U.S. Pat. Nos. 2,524,763 and 2,527,526 disclose orthodontic brackets which prior to attachment to the teeth are connected together in a strip. However, at the time of attachment, the brackets are detached from the strip and individually mounted to different teeth. Unlike the present invention, the individual brackets are not attached to more than one tooth.

U.S. Pat. No. 3,772,787 disclosed a double orthodontic bracket. Unlike the present invention, the double bracket is only attached to a single tooth.

SUMMARY OF THE INVENTION

The disadvantages and limitations of the prior art are obviated by the present invention. The orthodontic bracket of the present invention is attached to a plurality of teeth of a patient undergoing orthodontic treatment by a corresponding plurality of contoured surfaces formed in the bracket. One or more archwire attachments are formed in the bracket between different pairs of adjacent contoured surfaces. The archwire attachments are archwire slots which are individually formed in the bracket body from a slotted section of metal which has been bent. The length of the bent section measured along the dental arch is a function of the distance between the approximate centers in the mesial-distal direction of adjacent teeth to which the contoured surfaces are attached. When the bracket is attached to a patient's teeth, the archwire slots are disposed in the interproximal spaces located between the teeth.

The orthodontic bracket of the present invention has several advantages over the prior art. It allows the inclusion of the second molars in the orthodontic process because the direct bonding of the contoured surface of the bracket to a second molar does not require the second molars to be erupted to a point where an orthodontic band could be attached. Moreover, this allows mounting the buccal tube toward the rear of the mouth over the prior art. Additionally, the bracket's construction permits the attachment of the bracket closer to the gum line of the second molars which provides better anchorage and prevents rotation of the tooth because the bracket is mounted closer to the rotational axis of the tooth. The length of the bracket enhances visual orientation of the bracket during direct bonding to the teeth. The surface area of the plurality of contoured surfaces lessens the tendency of the bracket to slide on the buccal surfaces of the teeth during drying of an orthodontic cement used for bracket attachment. The location of the archwire slots in the interproximal areas between the teeth is in the area of least mastication force which lessens fatigue and breakage. The location of the archwire slot in the interproximal areas between the teeth lowers the profile of the bracket to lessen patient discomfort.

DESCRIPTION OF THE DRAWINGS

For a fuller understanding of the invention, reference is had to the following description taken in conjunction with the accompanying drawings, in which:

FIG. 1 is a top view of a bracket of the present invention before it has been shaped to fit the patient's teeth;

FIG. 2 is a front view of the bracket before it has been shaped to fit the patient's teeth;

FIG. 3 is a perspective view of the bracket attached to the teeth;

FIG. 4 is a perspective view of another embodiment of the bracket attached to the teeth.

DESCRIPTION OF THE PREFERRED EMBODIMENT

Referring to the drawings in detail, FIGS. 1 and 2 show the orthodontic bracket of the present invention before it has been shaped to the contours of an individual patient's teeth. As viewed from the top in FIG. 1 the unshaped bracket 11 is a thin elongated section of metal, which in the preferred embodiment is about 0.36 millimeters thick. Although in the preferred embodiment the bracket 11 is made of stainless steel, any suitable hard malleable corrosion resistant material may be utilized. FIG. 2 illustrates a side view of the bracket 11 before it has been shaped to fit the patient's mouth. Portions of the bracket 11 are widened to form buccal pads 13 which are designed to be attached to the buccal surfaces of the patient's teeth. Holes 15 in the pads 13 help insure better adhesive bonding between the pads and the teeth. Disposed between adjacent buccal pads 13 is a rectangular widened portion of the bracket which forms an interproximal bracket section 17. Bracket strips 19 are disposed between the buccal pads 13 and the interproximal bracket section 17. These strips 19 are relatively narrow and in the preferred embodiment measure only 2 millimeters in width while their length is a function of the size of the patient's mouth. The interproximal bracket section 17 and the adjacent bracket strips 19 comprise a bracket segment 21.

FIG. 3 illustrates the first embodiment of the present invention after it has been shaped and attached to the patient's teeth. The bracket 11 illustrated in FIGS. 1 and 2 is supplied in a plurality of lengths having different spacings between the buccal pads 13 to permit adapting it to use in different size mouths. After a plaster model of the patient's teeth is made, an appropriate length bracket 11 is chosen and then custom shaped to fit the patient's teeth. The buccal pads 13 are bent and shaped by an orthodontist or technician with the aid of the plaster model so that they form contoured surfaces that fit snuggly against the buccal surfaces of the teeth.

In this embodiment, the bracket 11 has three buccal pads 13 which are contoured to fit the first molar 25 and the first and second bicuspids 27 and 29 respectively. The point of attachment for each buccal pad 13 is preferably on the buccal surface of the tooth in the approximate center in the mesial-distal direction. Since the distance between the points of attachment on the teeth for each buccal pad 13 varies with the size of the mouth, the interproximal bracket section 17 is adjusted by bending or crimping to a rectangular cross-section so as to shorten the length of the bracket segment 21 between adjacent pads. The interproximal bracket section 17 is bent until the buccal pads 13 are spaced apart so that they can be affixed to the teeth at their proper points of attachment. A buccal tube 31 is then welded onto an interproximal bracket section 17 to provide anchorage for an archwire. In the first embodiment, the hollow cylindrical buccal tube 31 is mounted on the interproximal bracket section 17 between the first molar 25 and the second bicuspid 29 and extends in the mesial-distal direction. A buccal tube 31 is affixed to the respective brackets used for both the maxillary and mandibular arches. Head gear tubes 33, which are well known in the art, may also be welded to the interproximal bracket section 17 of the bracket 11 for the maxillary arch. Preferably, the width of the archwire slot 21 is such that an archwire will fit snuggly within the slot. However, archwires of any dimension and cross-section may be employed in the slot 23 depending upon the forces that are required to be applied to the teeth to be moved. Hooks 35 to which interarch elastics can be attached may be affixed to the bracket 11 if desired. In the preferred embodiment these hooks 35 are affixed to the head gear tubes 33 which are attached to the interproximal bracket section 17.

After the bracket 11 has been shaped and the buccal tube 31 and head gear tube 33 welded thereto it is ready to be affixed to the patient's teeth by a suitable adhesive such as GENIE and PROTECTO which are manufactured by Lee Pharmaceuticals. The constituents of GENIE and PROTECTO are disclosed respectively in patent applications Ser. Nos. 386,416 and 525,048.

FIG. 5 illustrates a second embodiment of the present invention. An additional buccal pad 13, interproximal bracket section 17 and bracket strip 19 is added to the bracket 11 to allow attachment to the second molar 37 in addition to the teeth used for attachment in the first embodiment. To take advantage of the attachment of the second molar to the bracket 11, the buccal tube 31 and head gear tube 33 are moved to the interproximal bracket section 17 between the first and second molars 25 and 37 respectively.

One of the major advantages of the present invention is that the contouring, shaping and welding necessary to ensure that the brackets fit the patient correctly can be done on a plaster model of the teeth at the inception of orthodontic treatment. After the model has been constructed, a properly trained technician can do the contouring and a properly trained dental assistant can band the brackets thereby reducing demands on the orthodontist once a diagnosis has been made.

Having the archwire slot 23 in the interproximal areas rather than the buccal surfaces reduces bracket projection in the buccal direction thereby lessening patient discomfort. It also lessens the possibility of bracket damage by reducing mastication forces on the bracket body.

The design of the bracket as an integral unit not only makes it easier to line up the bracket on the patient's teeth than it would be with a bracket consisting of many individual components, but it also lessens the chance of the bracket sliding while the adhesive is drying. Additionally, the interproximal bracket section 17 can function as hooks to which interarch traction elastics can be attached during orthodontic treatment.

Although the invention has been shown in connection with certain specific embodiments, it will be readily apparent to those skilled in the art that various changes in form and arrangement of components may be made without departing from the spirit and scope of the present invention. It is intended that these changes in form and arrangement fall within the scope of the claims.

What is claimed is:
1. An orthodontic bracket comprising:
   a. an elongated section of metal;
   b. a plurality of contoured surfaces formed in said elongated section of metal, each of said surfaces being respectively adapted to be attached to the buccal surface of a different tooth of a patient undergoing orthodontic treatment; and
   c. at least one attachment means which is adapted for attaching an archwire to said elongated section of metal.
2. An orthodontic bracket as recited in claim 1 wherein:
   a. said one or more means for attaching each comprise an arch-wire slot respectively formed between different adjacent pairs of contoured surfaces.
3. An orthodontic bracket as recited in claim 2 further comprising:
   a. a buccal tube attached to said elongated strip between two adjacent contoured surfaces.
4. An orthodontic bracket as recited in claim 3 further comprising:
   a. a head gear tube attached to said elongated strip between two adjacent contoured surfaces.
5. An orthodontic bracket as recited in claim 4 further comprising:
   a. a hook attached to said elongated strip between two adjacent contoured surfaces adapted to hold elastics used during orthodontic treatment of said patient.
6. An orthodontic bracket as recited in claim 1 further comprising:
   a. one or more bent sections respectively disposed between different pairs of adjacent contoured surfaces.
7. An orthodontic bracket as recited in claim 1 wherein:
   a. said one or more attachment means comprises one or more bent sections respectively disposd between different pairs of adjacent contoured surfaces, each of said bent sections having an archwire slot formed in it.
8. An orthodontic bracket as recited in claim 7 further comprising:
   a. a hook attached to a bent section, said hook being adapted to hold elastics used during orthodontic treatment of said patient.
9. An orthodontic bracket as recited in claim 7 further comprising:
   a. a buccal tube attached to said elongated strip between two adjacent contoured surfaces.

10. An orthodontic bracket as recited in claim 7 further comprising:
a. a head gear tube attached to said elongated strip between two adjacent contoured surfaces.

11. An orthodontic bracket as recited in claim 7 further comprising:
a. a hook attached to said head gear tube, said hook adapted to hold elastics used during orthodontic treatment of said patient.

12. An orthodontic bracket as recited in claim 5 wherein said elongated section of metal further comprises:
a. a first and second section of metal respectively disposed on different sides of each of said bent sections, said first and second sections being disposed between adjacent contoured surfaces; and wherein
b. said bent sections have a predetermined length measured along the dental arch of the patient which is a function of the distance between the points of attachment between adjacent contoured surfaces.

13. An orthodontic bracket as recited in claim 12 wherein:
a. said bent section contains four right angle bends.

14. An orthodontic bracket as recited in claim 1 wherein:
a. said contoured surfaces have holes cut therein.

15. A process for fitting an orthodontic bracket having an elongated section of metal, a plurality of contoured surfaces formed therein which each are respectively adapted to be attached to the buccal surface of a different tooth of a patient undergoing orthodontic treatment and at least one attachment means which is adapted for attaching an archwire to said elongated section of metal comprising:
a. making a plaster mold of a patient's teeth;
b. bending said elongated section of metal between said contoured surfaces so that the distance between adjacent contoured surfaces is approximately equal to the distance between respective centers of the buccal surfaces of the teeth to which the adjacent contoured surfaces are adapted to be attached.

16. The process of claim 15 further comprising:
a. attaching said orthodontic bracket to the patient's teeth at said contoured surfaces.

* * * * *